US00H002071H

(19) United States

(12) Statutory Invention Registration (10) Reg. No.: US H2071 H

Peery et al. (43) Published: Jul. 1, 2003

(54) *STREPTOCOCCUS PNEUMONIAE* GENE HI0454

(75) Inventors: Robert Brown Peery, Brownsburg, IN (US); Paul Luther Skatrud, Greenwood, IN (US); Michele Louise Young Bellido, Indianapolis, IN (US); Patti Jean Treadway, Greenwood, IN (US)

(73) Assignee: Eli Lilly and Company, Indianapolis, IN (US)

(21) Appl. No.: 08/987,147

(22) Filed: Dec. 8, 1997

Related U.S. Application Data

(60) Provisional application No. 60/036,281, filed on Dec. 13, 1996.

(51) Int. Cl.[7] ..... C12P 21/04

(52) U.S. Cl. ..... 435/71.2; 435/69.1; 435/69.3; 435/71.1; 435/440; 435/471; 435/252.3; 435/254.11; 435/257.2; 435/320.1; 435/822; 536/23.1; 536/23.7; 536/24.32

(58) Field of Search ..... 435/320.1, 69.1, 435/69.3, 71.1, 71.2, 410, 471, 822, 252.3, 254.11, 257.2; 536/23.1, 23.7, 24.32

(56) References Cited

PUBLICATIONS

Lindler et al. Journal of Bacteriology, Jul. 1987 169(7): 3199–3208.*

Gibco BRL, Catalogue and Reference Guide 1992, p. 292.*

Stratagene 1991 Product Catalog, p. 66.*

Boehanger Mannheim Biochemicals, 1991 Catalog p. 557.*

Promega, 1993/94 Catalog, pp. 90–91.*

New England Biolabs catalog 1986/87, pp. 60–62.*

Fleischmann, et al. "Whole–Genome Random Sequencing and Assembly of *Haemophilus influenzae* Rd." *Science* 269:496–512 (July 28, 1995).

* cited by examiner

*Primary Examiner*—Michael J. Carone

*Assistant Examiner*—Aileen B. Felton

(74) *Attorney, Agent, or Firm*—Thomas D. Webster; Raymond S. Parker, III; Charles E. Cohen

(57) ABSTRACT

The invention provides isolated nucleic acid compounds encoding the 454 gene of *Streptococcus pneumoniae*. Also provided are vectors and transformed host cells for expressing the encoded protein, and a method for identifying compounds that bind and/or inhibit said protein.

26 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

*STREPTOCOCCUS PNEUMONIAE* GENE HI0454

This application claims the benefit of U.S. Provisional Application No. 60/036,281, filed Dec. 13, 1996.

BACKGROUND OF THE INVENTION

This invention provides isolated DNA sequences, proteins encoded thereby, and methods of using said DNA and protein in a variety of applications.

Widespread antibiotic resistance in common pathogenic bacterial species has justifiably alarmed the medical and research communities. Frequently, resistant organisms are co-resistant to several antibacterial agents. Penicillin resistance in *Streptococcus pneumoniae* has been particularly problematic. This organism causes upper respiratory tract infections. Modification of a penicillin-binding protein (PBP) underlies resistance to penicillin in the majority of cases. Combating resistance to antibiotic agents will require research into the molecular biology of pathogenic organisms. The goal of such research will be to identify new antibacterial agents.

While researchers continue to develop antibiotics effective against a number of microorganisms, *Streptococcus pneumoniae* has been more refractory. In part, this is because *Streptococcus pneumoniae* is highly recombinogenic and readily takes up exogenous DNA from its surroundings. Thus, there is a need for new antibacterial compounds and new targets for antibacterial therapy in *Streptococcus pneumoniae.*

BRIEF SUMMARY OF THE INVENTION

The present invention relates to an isolated gene and encoded protein from *S. pneumoniae*. The invention enables: (1) preparation of probes and primers for use in hybridizations and PCR amplifications, (2) production of proteins and RNAs encoded by said gene and related nucleic acids, and (3) methods to identify compounds that bind and/or inhibit said protein(s).

In one embodiment the present invention relates to an isolated nucleic acid molecule encoding a protein designated 454.

In another embodiment, the invention relates to a nucleic acid molecule comprising the nucleotide sequence identified as SEQ ID NO:1, SEQ ID NO:3, or SEQ ID NO:4.

In another embodiment, the present invention relates to a nucleic acid that encodes SEQ ID NO:2.

In another embodiment the present invention relates to an isolated protein molecule, wherein said protein molecule comprises the sequence identified as SEQ ID NO:2.

In yet another embodiment, the present invention relates to a recombinant DNA vector that incorporates the 454 gene in operable linkage to gene expression sequences enabling the gene to be transcribed and translated in a host cell.

In still another embodiment the present invention relates to host cells that have been transformed or transfected with the cloned 454 gene such that said gene is expressed in the host cell.

This invention also provides a method of determining whether a nucleic acid sequence of the present invention, or fragment thereof, is present in a sample, comprising contacting the sample, under suitable hybridization conditions, with a nucleic acid probe of the present invention.

In a still further embodiment, the present invention relates to a method for identifying compounds that bind and/or inhibit the 454 protein.

DETAILED DESCRIPTION OF THE INVENTION

"ORF" (i.e. "open reading frame") designates a region of genomic DNA beginning with a Met or other initiation codon and terminating with a translation stop codon, that potentially encodes a protein product. "Partial ORF" means a portion of an ORF as disclosed herein such that the initiation codon, the stop codon, or both are not disclosed.

"Consensus sequence" refers to an amino acid or nucleotide sequence that may suggest the biological function of a protein, DNA, or RNA molecule. Consensus sequences are identified by comparing proteins, RNAs, and gene homologues from different species.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

"Essential genes" or "essential ORFs" or "essential proteins" refer to genomic information or the protein(s) or RNAs encoded thereby, that when disrupted by knockout mutation, or by other mutation, result in a loss of viability of cells harboring said mutation.

"Non-essential genes" or "non-essential ORFs" or "non-essential proteins" refer to genomic information or the protein(s) or RNAs encoded therefrom which when disrupted by knockout mutation, or other mutation, do not result in a loss of viability of cells harboring said mutation.

"Minimal gene set" refers to a genus comprising about 256 genes conserved among different bacteria such as *M. genitalium* and *H. influenzae*. The minimal gene set may be necessary and sufficient to sustain life. See e.g. A. Mushegian and E. Koonin, "A minimal gene set for cellular life derived by comparison of complete bacterial genomes" Proc. Nat. Acad. Sci. 93, 10268–273 (1996).

"Knockout mutant" or "knockout mutation" as used herein refers to an in vitro engineered disruption of a region of native chromosomal DNA, typically within a protein coding region, such that a foreign piece of DNA is inserted within the native sequence. A knockout mutation occurring in a protein coding region prevents expression of the wild-type protein. This usually leads to loss of the function provided by the protein. A "knockout cassette" refers to a fragment. of native chromosomal DNA having cloned therein a foreign piece of DNA that may provide a selectable marker.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refer to the capacity of purine and pyrimidine nucleotides to associate through hydrogen bonding to form double stranded nucleic acid molecules. The following base pairs are related by complementarity: guanine and cytosine; adenine and thymine; and adenine and uracil. As used herein, "complementary" applies to all base pairs comprising two single-stranded nucleic acid molecules. "Partially complementary" means one of two single-stranded nucleic acid molecules is shorter than the other, such that one of the molecules remains partially single-stranded.

"Oligonucleotide" refers to a short nucleotide chain comprising from about 2 to about 25 nucleotides.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which can be used to hybridize with another nucleic acid compound.

The term "hybridization" or "hybridize" as used herein refers to the process by which a single-stranded nucleic acid molecule joins with a complementary strand through nucleotide base pairing.

"Substantially purified" as used herein means a specific isolated nucleic acid or protein, or fragment thereof, in which substantially all contaminants (i.e. substances that differ from said specific molecule) have been separated from said nucleic acid or protein. For example, a protein may, but not necessarily, be "substantially purified" by the IMAC method as described herein.

"Selective hybridization" refers to hybridization under conditions of high stringency. The degree of hybridization between nucleic acid molecules depends upon, for example, the degree of complementarity, the stringency of hybridization, and the length of hybridizing strands.

The term "stringency" relates to nucleic acid hybridization conditions. High stringency conditions disfavor non-homologous base pairing. Low stringency conditions have the opposite effect. Stringency may be altered, for example, by changes in temperature and salt concentration. Typical high stringency conditions comprise hybridizing at 50° C. to 65° C. in 5×SSPE and 50% formamide, and washing at 50° C. to 65° C. in 0.5×SSPE; typical low stringency conditions comprise hybridizing at 35° C. to 37° C. in 5×SSPE and 40% to 45% formamide and washing at 42° C. in 1×–2×SSPE.

"SSPE" denotes a hybridization and wash solution comprising sodium chloride, sodium phosphate, and EDTA, at pH 7.4. A 20×solution of SSPE is made by dissolving 174 g of NaCl, 27.6 g of $NaH_2PO4$. $H_2O$, and 7.4 g of EDTA in 800 ml of $H_2O$. The pH is adjusted with NaOH and the volume brought to 1 liter.

"SSC" denotes a hybridization and wash solution comprising sodium chloride and sodium citrate at pH 7. A 20×solution of SSC is made by dissolving 175 g of NaCl and 88 g of sodium citrate in 800 ml of $H_2O$. The volume is brought to 1 liter after adjusting the pH with 10N NaOH.

DETAILED DESCRIPTION OF THE INVENTION

The 454 gene disclosed herein (SEQ ID NO:1) and related nucleic acids (viz. SEQ ID NO:3 and SEQ ID NO:4) encode an essential protein that is a member of the minimal gene set.

Cells that carry knockout mutations in the 454 gene lose viability. Loss of viability suggests that the encoded protein may be essential for cell viability.

In one embodiment, the proteins of this invention are purified, and used in a screen to identify compounds that bind and/or inhibit the activity of said proteins. A variety of suitable screens are contemplated for this purpose. For example, the protein(s) can be labeled by known techniques, such as radiolabeling or fluorescent tagging, or by labeling with biotin/avidin. Thereafter, binding of a test compound to a labeled protein can be determined by any suitable means, well known to the skilled artisan.

Skilled artisans will recognize that the DNA molecules of this invention, or fragments thereof, can be generated by general cloning methods. PCR amplification using oligonucleotide primers targeted to any suitable region of SEQ ID NO:1 is preferred. Methods for PCR amplification are widely known in the art. See e.g. *PCR Protocols: A Guide to Method and Application*, Ed. M. Innis et al., Academic Press (1990) or U.S. Pat. No. 4,889,818, which hereby is incorporated by reference. A PCR comprises DNA, suitable enzymes, primers, and buffers, and is conveniently carried out in a DNA Thermal Cycler (Perkin Elmer Cetus, Norwalk, Conn.). A positive PCR result is determined by, for example, detecting an appropriately-sized DNA fragment following agarose gel electrophoresis.

The DNAs of the present invention may also be produced using synthetic methods well known in the art. (See, e.g., E. L. Brown, R. Belagaje, M. J. Ryan, and H. G. Khorana, *Methods in Enzymology*, 68:109–151 (1979)). An apparatus such as the Applied Biosystems Model 380A or 380B DNA synthesizers (Applied Biosystems, Inc., 850 Lincoln Center Drive, Foster City, Calif. 94404) may be used to synthesize DNA. Synthetic methods rely upon phosphotriester chemistry [See, e.g., M. J. Gait, ed., *Oligonucleotide Synthesis, A Practical Approach*, (1984)], or phosphoramidite chemistry.

Protein Production Methods

The present invention relates further to substantially purified proteins encoded by the gene disclosed herein.

Skilled artisans will recognize that proteins can be synthesized by different methods, for example, chemical methods or recombinant methods, as described in U.S. Pat. No. 4,617,149, which hereby is incorporated by reference.

The principles of solid phase chemical synthesis of polypeptides are well known in the art and may be found in general texts relating to this area. See, e.g., H. Dugas and C. Penney, *Bioorganic Chemistry* (1981) Springer-Verlag, N.Y., 54–92. Peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

The proteins of the present invention can also be made by recombinant DNA methods. Recombinant methods are preferred if a high yield is desired. Recombinant methods involve expressing the cloned gene in a suitable host cell. The gene is introduced into the host cell by any suitable means, well known to those skilled in the art. While chromosomal integration of the cloned gene is within the scope of the present invention, it is preferred that the cloned gene be maintained extra-chromosomally, as part of a vector in which the gene is in operable-linkage to a promoter.

Recombinant methods can also be used to overproduce a membrane-bound or membrane-associated protein. In some cases, membranes prepared from recombinant cells expressing such proteins provide an enriched source of the protein.

Expressing Recombinant Proteins in Procaryotic and Eucaryotic Host Cells

Procaryotes are generally used for cloning DNA sequences and for constructing vectors. For example, the *Escherichia coli* K12 strain 294 (ATCC No. 31446) is particularly useful for expression of foreign proteins. Other strains of *E. coli*, bacilli such as *Bacillus subtilis*, enterobacteriaceae such as *Salmonella typhimurium* or *Serratia marcescans*, various Pseudomonas species may also be employed as host cells in cloning and expressing the recombinant proteins of this invention. Also contemplated are various strains of Streptococcus and Streptocmyces.

For effective recombinant protein production, a gene must be linked to a promoter sequence. Suitable bacterial promoters include b-lactamase [e.g. vector pGX2907, ATCC 39344, contains a replicon and b-lactamase gene], lactose systems [Chang et al., *Nature* (London), 275:615 (1978); Goeddel et al., *Nature* (London), 281:544 (1979)], alkaline phosphatase, and the tryptophan (trp) promoter system [vector pATH1 (ATCC 37695)] designed for the expression of a trpE fusion protein. Hybrid promoters such as the tac promoter (isolatable from plasmid pDR540, ATCC-37282) are also suitable. Promoters for use in bacterial systems also will contain a Shine-Dalgarno sequence, operably linked to the DNA encoding the desired polypeptides. These examples are illustrative rather than limiting.

A variety of mammalian cells and yeasts are also suitable hosts. The yeast *Saccharomyces cerevisiae* is commonly used. Other yeasts, such as *Kluyveromyces lactis*, are also suitable. For expression of recombinant genes in Saccharomyces, the plasmid YRp7 (ATCC-40053), for example, may be used. See, e.g., L. Stinchcomb, et al., *Nature*, 282:39 (1979); J. Kingsman et al., *Gene*, 7:141 (1979); S. Tschemper et al., *Gene*, 10:157 (1980). Plasmid YRp7 contains the TRP1 gene, a selectable marker for a trp1 mutant.

Purification of Recombinantly-Produced Protein

An expression vector carrying a nucleic acid or gene of the present invention is transformed or transfected into a suitable host cell using standard methods. Cells that contain the vector are propagated under conditions suitable for expression of a recombinant protein. For example, if the gene is under the control of an inducible promoter, then suitable growth conditions would incorporate the appropriate inducer. The recombinantly-produced protein may be purified from cellular extracts of transformed cells by any suitable means.

In a preferred process for protein purification a gene is modified at the 5' end, or at some other position, such that the encoded protein incorporates several histidine residues (viz. "histidine tag"). This "histidine tag" enables "immobilized metal ion affinity chromatography" (IMAC), a single-step protein purification method described in U.S. Pat. No. 4,569,794, which hereby is incorporated by reference. The IMAC method enables isolation of substantially pure protein starting from a crude cellular extract.

As skilled artisans will recognize, owing to the degeneracy of the code, the proteins of the invention can be encoded by a large genus of different nucleic acid sequences. This invention further comprises said genus.

The ribonucleic acid compounds of the invention may be prepared using the polynucleotide synthetic methods discussed supra, or they may be prepared enzymatically using RNA polymerase to transcribe a DNA template.

The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5' end of a template. See, J. Sambrook, et al., supra, at 18.82–18.84.

This invention also provides nucleic acids that are complementary to the sequences disclosed herein.

The present invention also provides probes and primers, useful for a variety of molecular biology techniques including, for example, hybridization screens of genomic or subgenomic libraries, or detection and quantification of mRNA species as a means to analyze gene expression. A nucleic acid compound is provided comprising any of the sequences disclosed herein, or a complementary sequence thereof, or a fragment thereof, which is at least 15 base pairs in length, and which will hybridize selectively to *Streptococcus pneumoniae* DNA or mRNA. Preferably, the 15 or more base pair compound is DNA. A probe or primer length of at least 15 base pairs is dictated by theoretical and practical considerations. See e.g. B. Wallace and G. Miyada, "Oligonucleotide Probes for the Screening of Recombinant DNA Libraries," In *Methods in Enzymology*, Vol. 152, 432–442, Academic Press (1987).

The probes and primers of this invention can be prepared by methods well known to those skilled in the art (See e.g. Sambrook et al. supra). In a preferred embodiment the probes and primers are synthesized by the polymerase chain reaction (PCR).

The present invention also relates to recombinant DNA cloning vectors and expression vectors comprising the nucleic acids of the present invention. Preferred nucleic acid vectors are those that comprise DNA. The skilled artisan understands that choosing the most appropriate cloning vector or expression vector depends on the availability of restriction sites, the type of host cell into which the vector is to be transfected or transformed, the purpose of transfection or transformation (e.g., stable transformation as an extrachromosomal element, or integration into a host chromosome), the presence or absence of readily assayable or selectable markers (e.g., antibiotic resistance and metabolic markers of one type and another), and the number of gene copies desired in the host cell.

Suitable vectors comprise RNA viruses, DNA viruses, lytic bacteriophages, lysogenic bacteriophages, stable bacteriophages, plasmids, viroids, and the like. The most preferred vectors are plasmids.

Host cells harboring the nucleic acids disclosed herein are also provided by the present invention. A preferred host is *E. coli* transfected or transformed with a vector comprising a nucleic acid of the present invention.

The invention also provides a host cell capable of expressing a gene described herein, said method comprising transforming or otherwise introducing into a host cell a recombinant DNA vector comprising an isolated DNA sequence that encodes said gene. The preferred host cell is any strain of *E. coli* that can accommodate high level expression of an exogenously introduced gene. Transformed host cells are cultured under conditions well known to skilled artisans, such that said gene is expressed, thereby producing the encoded protein in the recombinant host cell.

To discover compounds having antibacterial activity, one can look for agents that inhibit cell growth and/or viability by, for example, inhibiting enzymes required for cell wall biosynthesis, and/or by identifying agents that interact with membrane proteins. A method for identifying such compounds comprises contacting a suitable protein or membrane preparation with a test compound and monitoring by any suitable means an interaction and/or inhibition of a protein of this invention.

For example, the instant invention provides a screen for compounds that interact with the proteins of the invention, said screen comprising:

a) preparing a protein, or membranes enriched in a protein;

b) exposing the protein or membranes to a test compound; and c) detecting an interaction of a protein with said compound by any suitable means.

The screening method of this invention may be adapted to automated procedures such as a PANDEX® (Baxter-Dade Diagnostics) system, allowing for efficient high-volume screening of compounds.

In a typical screen, a protein is prepared as described herein, preferably using recombinant DNA technology. A test compound is introduced into a reaction vessel containing said protein. The reaction/interaction of said protein and said compound is monitored by any suitable means. In a preferred method, a radioactively-labeled or chemically-labeled compound or protein is used. A specific association between the test compound and protein is monitored by any suitable means.

In such a screening protocol 454 is prepared as described herein, preferably using recombinant DNA technology. A test compound is introduced into a reaction vessel containing the 454 protein or fragment thereof. Binding of 454 by a test compound is determined by any suitable means. For example, in one method radioactively-labeled or chemically-labeled test compound may be used. Binding of the protein by the compound is assessed, for example, by quantifying bound label versus unbound label using any suitable method. Binding of a test compound may also be carried out by a method disclosed in U.S. Pat. No. 5,585,277, which hereby is incorporated by reference. In this method, binding of a test compound to a protein is assessed by monitoring the ratio of folded protein to unfolded protein, for example by monitoring sensitivity of said protein to a protease, or amenability to binding of said protein by a specific antibody against the folded state of the protein.

The foregoing screening methods are useful for identifying a ligand of a 454 protein, perhaps as a lead to a pharmaceutical compound for modulating the state of differentiation of an appropriate tissue. A ligand that binds 454, or related fragment thereof, is identified, for example, by combining a test ligand with 454 under conditions that cause the protein to exist in a ratio of folded to unfolded states. If the test ligand binds the folded state of the protein, the relative amount of folded protein will be higher than in the case of a test ligand that does not bind the protein. The ratio of protein in the folded versus unfolded state is easily determinable by, for example, susceptibility to digestion by a protease, or binding to a specific antibody, or binding to chaperonin protein, or binding to any suitable surface.

The following examples more fully describe the present invention. Those skilled in the art will recognize that the particular reagents, equipment, and procedures described are merely illustrative and are not intended to limit the present invention in any manner.

EXAMPLE 1

Production of a Vector for Expressing *S. pneumoniae* 454 Gene in a Host Cell An expression vector suitable for expressing *S. pneumoniae* 454 in a variety of procaryotic host cells, such as *E. coli*, is easily made. The vector contains an origin of replication (Ori), an ampicillin resistance gene (Amp) useful for selecting cells which have incorporated the vector following a tranformation procedure, and further comprises the T7 promoter and T7 terminator sequences in operable linkage to the coding region. Plasmid pET11A (obtained from Novogen, Madison, Wis.) is a suitable parent plasmid. pET11A is linearized by restriction with endonucleases NdeI and BamHI. Linearized pET11A is ligated to a DNA fragment bearing NdeI and BamHI sticky ends and comprising the coding region of the *S. pneumoniae* 454 gene (SEQ ID NO:1). The coding region for 454 is easily produced by PCR technology using suitably designed primers to the ends of the coding region specified in SEQ ID NO:1.

The 454 gene used in this construction is slightly modified at the 5' end (amino terminus of encoded protein) in order to simplify purification of the encoded protein product. For this purpose, an oligonucleotide encoding 8 histidine residues is inserted after the ATG start codon. Placement of the histidine residues at the amino terminus of the encoded protein serves to enable the IMAC one-step protein purification procedure.

EXAMPLE 2

Recombinant Expression and Purification of a Protein Encoded by *S. pneumoniae* 454 Gene An expression vector that carries the 454 Gene from the *S. pneumoniae* genome as disclosed herein and which is operably-linked to an expression promoter is transformed into *E. coli* BL21 (DE3) (hsdS gal lcIts857 ind1Sam7nin5lacUV5-T7gene 1) using standard methods (see Example 4). Transformants, selected for resistance to ampicillin, are chosen at random and tested for the presence of the vector by agarose gel electrophoresis using quick plasmid preparations. Colonies which contain the vector are grown in L broth and the protein product encoded by the vector-borne ORF is purified by immobilized metal ion affinity chromatography (IMAC), essentially as described in U.S. Pat. No. 4,569,794.

Briefly, the IMAC column is prepared as follows. A metal-free chelating resin (e.g. Sepharose 6B IDA, Pharmacia) is washed in distilled water to remove preservative substances and infused with a suitable metal ion [e.g. Ni(II), Co(II), or Cu(II)] by adding a 50 mM metal chloride or metal sulfate aqueous solution until about 75% of the interstitial spaces of the resin are saturated with colored metal ion. The column is then ready to receive a crude cellular extract containing the recombinant protein product.

After removing unbound proteins and other materials by washing the column with any suitable buffer, pH 7.5, the bound protein is eluted in any suitable buffer at pH 4.3, or preferably with an imidizole-containing buffer at pH 7.5.

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
(A) LENGTH: 774 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: CDS
(B) LOCATION: 1..771

(xi) SEQUENCE DESCRIPTION: SEQ ID NO:1:

```
ATG ATT TTT GAT ACA CAT ACA CAC TTG AAT GTA GAA GAA TTT GCA GGT       48
Met Ile Phe Asp Thr His Thr His Leu Asn Val Glu Glu Phe Ala Gly
  1               5                  10                  15

CGT GAG GCA GAA GAA ATT GCC TTG GCT GCT GAG ATG GGT GTG ACA CAG       96
Arg Glu Ala Glu Glu Ile Ala Leu Ala Ala Glu Met Gly Val Thr Gln
             20                  25                  30

ATG AAT ATT GTT GGT TTT GAT AAA CCG ACG ATT GAG CAT GCC TTG GAG      144
Met Asn Ile Val Gly Phe Asp Lys Pro Thr Ile Glu His Ala Leu Glu
         35                  40                  45

TTG GTA GAT GAG TAT GAG CAG CTC TAT GCG ACT ATT GGT TGG CAT CCT      192
Leu Val Asp Glu Tyr Glu Gln Leu Tyr Ala Thr Ile Gly Trp His Pro
     50                  55                  60

ACA GAA GCT GGT ACT TAT ACA GAG GAA GTT GAG GCT TAC TTG TTG GAT      240
Thr Glu Ala Gly Thr Tyr Thr Glu Glu Val Glu Ala Tyr Leu Leu Asp
 65                  70                  75                  80

AAG TTA AAA CAT TCC AAG GTT GTG GCT TTA GGT GAA ATT GGC TTA GAC      288
Lys Leu Lys His Ser Lys Val Val Ala Leu Gly Glu Ile Gly Leu Asp
                 85                  90                  95

TAC CAT TGG ATG ACA GCG CCC AAA GAG GTG CAG GAG CAG GTT TTT CGC      336
Tyr His Trp Met Thr Ala Pro Lys Glu Val Gln Glu Gln Val Phe Arg
            100                 105                 110

CGT CAG ATT CAG CTA TCT AAG GAC TTG GAT TTG CCT TTT GTT GTC CAT      384
Arg Gln Ile Gln Leu Ser Lys Asp Leu Asp Leu Pro Phe Val Val His
        115                 120                 125

ACC CGT GAT GCG CTG GAA GAT ACC TAT GAG ATT ATC AAG AGT GAG GGC      432
Thr Arg Asp Ala Leu Glu Asp Thr Tyr Glu Ile Ile Lys Ser Glu Gly
    130                 135                 140

GTT GGT CCT CGT GGT GGT ATC ATG CAT TCA TTT TCA GGG ACG CTT GAG      480
Val Gly Pro Arg Gly Gly Ile Met His Ser Phe Ser Gly Thr Leu Glu
145                 150                 155                 160

TGG GCA GAG AAG TTT GTG GAT CTT GGT ATG ACC ATT TCC TTC TCA GGA      528
Trp Ala Glu Lys Phe Val Asp Leu Gly Met Thr Ile Ser Phe Ser Gly
                165                 170                 175

GTG GTG ACC TTC AAG AAG GCA ACT GAC CTC CAA GAA GCA GCT AAA GAG      576
Val Val Thr Phe Lys Lys Ala Thr Asp Leu Gln Glu Ala Ala Lys Glu
            180                 185                 190

TTA CCT TTG GAC AAG ATG TTG GTA GAA ACA GAT GCG CCT TAC TTA GCA      624
Leu Pro Leu Asp Lys Met Leu Val Glu Thr Asp Ala Pro Tyr Leu Ala
        195                 200                 205
```

-continued

```
CCT GTA CCC AAG CGT GGT CGT GAA AAT AAA ACA GCC TAT ACT CGC TAT      672
Pro Val Pro Lys Arg Gly Arg Glu Asn Lys Thr Ala Tyr Thr Arg Tyr
    210                 215                 220

GTG GTC GAC TTT ATC GCT GAC TTG CGT GGT ATG ACG ACA GAA GAG CTG      720
Val Val Asp Phe Ile Ala Asp Leu Arg Gly Met Thr Thr Glu Glu Leu
225                 230                 235                 240

GCG GTA GCA ACG ACT GCA AAT GCA GAA CGC ATT TTT GGA TTG GAC AGC      768
Ala Val Ala Thr Thr Ala Asn Ala Glu Arg Ile Phe Gly Leu Asp Ser
                245                 250                 255

AAG TAA                                                              774
Lys
```

(2) INFORMATION FOR SEQ ID NO:2:

(i) SEQUENCE CHARACTERISTICS:
(A) LENGTH: 257 amino acids
(B) TYPE: amino acid
(D) TOPOLOGY: linear (ii) MOLECULE TYPE: protein (xi) SEQUENCE DESCRIPTION: SEQ ID NO:2:

```
Met Ile Phe Asp Thr His Thr His Leu Asn Val Glu Glu Phe Ala Gly
  1               5                  10                  15

Arg Glu Ala Glu Glu Ile Ala Leu Ala Ala Glu Met Gly Val Thr Gln
             20                  25                  30

Met Asn Ile Val Gly Phe Asp Lys Pro Thr Ile Glu His Ala Leu Glu
         35                  40                  45

Leu Val Asp Glu Tyr Glu Gln Leu Tyr Ala Thr Ile Gly Trp His Pro
     50                  55                  60

Thr Glu Ala Gly Thr Tyr Thr Glu Glu Val Glu Ala Tyr Leu Leu Asp
 65                  70                  75                  80

Lys Leu Lys His Ser Lys Val Val Ala Leu Gly Glu Ile Gly Leu Asp
                 85                  90                  95

Tyr His Trp Met Thr Ala Pro Lys Glu Val Gln Glu Gln Val Phe Arg
            100                 105                 110

Arg Gln Ile Gln Leu Ser Lys Asp Leu Asp Leu Pro Phe Val Val His
        115                 120                 125

Thr Arg Asp Ala Leu Glu Asp Thr Tyr Glu Ile Ile Lys Ser Glu Gly
    130                 135                 140

Val Gly Pro Arg Gly Gly Ile Met His Ser Phe Ser Gly Thr Leu Glu
145                 150                 155                 160

Trp Ala Glu Lys Phe Val Asp Leu Gly Met Thr Ile Ser Phe Ser Gly
                165                 170                 175

Val Val Thr Phe Lys Lys Ala Thr Asp Leu Gln Glu Ala Ala Lys Glu
            180                 185                 190

Leu Pro Leu Asp Lys Met Leu Val Glu Thr Asp Ala Pro Tyr Leu Ala
        195                 200                 205

Pro Val Pro Lys Arg Gly Arg Glu Asn Lys Thr Ala Tyr Thr Arg Tyr
    210                 215                 220

Val Val Asp Phe Ile Ala Asp Leu Arg Gly Met Thr Thr Glu Glu Leu
225                 230                 235                 240

Ala Val Ala Thr Thr Ala Asn Ala Glu Arg Ile Phe Gly Leu Asp Ser
                245                 250                 255

Lys
```

-continued (2) INFORMATION FOR SEQ ID NO:3:

(i) SEQUENCE CHARACTERISTICS:
(A) LENGTH: 771 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

AUGAUUUUUG AUACACAUAC ACACUUGAAU GUAGAAGAAU UUGCAGGUCG UGAGGCAGAA 60

GAAAUUGCCU UGGCUGCUGA GAUGGGUGUG ACACAGAUGA AUAUUGUUGG UUUUGAUAAA 120

CCGACGAUUG AGCAUGCCUU GGAGUUGGUA GAUGAGUAUG AGCAGCUCUA UGCGACUAUU 180

GGUUGGCAUC CUACAGAAGC UGGUACUUAU ACAGAGGAAG UUGAGGCUUA CUUGUUGGAU 240

AAGUUAAAAC AUUCCAAGGU UGUGGCUUUA GGUGAAAUUG GCUUAGACUA CCAUUGGAUG 300

ACAGCGCCCA AAGAGGUGCA GGAGCAGGUU UUUCGCCGUC AGAUUCAGCU AUCUAAGGAC 360

UUGGAUUUGC CUUUUGUUGU CCAUACCCGU GAUGCGCUGG AAGAUACCUA UGAGAUUAUC 420

AAGAGUGAGG GCGUUGGUCC UCGUGGUGGU AUCAUGCAUU CAUUUUCAGG GACGCUUGAG 480

UGGGCAGAGA AGUUUGUGGA UCUUGGUAUG ACCAUUUCCU UCUCAGGAGU GGUGACCUUC 540

AAGAAGGCAA CUGACCUCCA AGAAGCAGCU AAAGAGUUAC CUUUGGACAA GAUGUUGGUA 600

GAAACAGAUG CGCCUUACUU AGCACCUGUA CCCAAGCGUG GUCGUGAAAA UAAAACAGCC 660

UAUACUCGCU AUGUGGUCGA CUUUAUCGCU GACUUGCGUG GUAUGACGAC AGAAGAGCUG 720

GCGGUAGCAA CGACUGCAAA UGCAGAACGC AUUUUUGGAU UGGACAGCAA G 771

(2) INFORMATION FOR SEQ ID NO:4:

(i) SEQUENCE CHARACTERISTICS:
(A) LENGTH: 852 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

GCCGTCATAA TCATGCGCCG AATCCGTCCC CATTAAAATC TGGGTCTGTA AAGACAATGA 60

CTCCATGACG TTGGTGTAGA CGCTGAATCC GCTCTATGTC CTGGTCATTG ATGGCAGAAC 120

CTCGAGTCTC ATAGGTCTCC ACATCGAAAT AACGCTTGAG ATTGACCGTA TCATCACGAC 180

CTTCAACCAC GATAACTTGG GAAATTCTCT CTTTCATTAC TTGCTGTCCA ATCCCAAAAA 240

TGCGTTCTGC ATTTGCAGTC GTTGCTACCG CCAGCTCTTC TGTCGTCATA CCACGCAAGT 300

CAGCGATAAA GTCGACCACA TAGCGAGTAT AGGCTGTTTT ATTTTCACGA CCACGCTTGG 360

GTACAGGTGC TAAGTAAGGC GCATCTGTTT CTACCAACAT CTTGTCCAAA GGTAACTCTT 420

TAGCTGCTTC TTGGAGGTCA GTTGCCTTCT TGAAGGTCAC CACTCCTGAG AAGGAAATGG 480

TCATACCAAG ATCCCGGTAC CGAGCCCACT CAAGCGTCCC TGAAAATGAA TGCATGATAC 540

CACCACGAGG ACCAACGCCC TCACTCTTGA TAATCTCATA GGTATCTTCC AGCGCATCAC 600

-continued

```
GGGTATGGAC AACAAAAGGC AAATCCAAGT CCTTAGATAG CTGAATCTGA CGGCGAAAAA    660

CCTGCTCCTG CACCTCTTGG GCGCTGTCAT CCAATGGTAG TCTAAGCCAA TTTCACCTAA    720

AGCCACAACC TTGGAATGTT TTAACTTATC CAACAAGTAA GCCTCAACTT CCTCTGTATA    780

AGTACCAGCT TCTGTAGGAT GCCAACCAAT AGTCGCATAG AGCTGCTCAT ACTCATCTAC    840

CAAACTCCAA GG                                                        852
```

We claim:

1. An isolated nucleic acid fragment encoding a protein having the amino acid sequence of SEQ ID NO:2.

2. An isolated nucleic acid fragment, wherein said fragment has a sequence selected from the group consisting of:

(a) SEQ ID NO: 1;

(b) SEQ ID NO: 3;

(c) a nucleic acid fragment that encodes the same protein as (a) or (b), but which is degenerate in accordance with the degeneracy of the genetic code; and (d) a nucleic acid fragment fully complementary to (a), (b), or (c).

3. The isolated nucleic acid fragment of claim 2, wherein the sequence of said fragment is selected from the group consisting of SEQ ID NO:1, a nucleic acid fragment that encodes the same protein as SEQ ID NO:1, but which is degenerate in accordance with the degeneracy of the genetic code, and a nucleic acid fragment fully complementary to either of the foregoing.

4. The isolated nucleic acid fragment of claim 2, wherein the sequence of said fragment is selected from the group consisting of SEQ ID NO:3, a nucleic acid fragment that encodes the same protein as SEO ID NO:3, but which is degenerate in accordance with the degeneracy of the genetic code, and a nucleic acid fragment fully complementary to either of the foregoing.

5. A vector comprising an isolated nucleic acid fragment of claim 2.

6. A host cell containing the vector of claim 5.

7. The vector of claim 5, wherein said isolated nucleic acid fragment is SEQ ID NO:1, operably linked to a promoter sequence.

8. A method for constructing a recombinant host cell having the potential to express SEQ ID NO:2, said method comprising introducing into said host cell by any suitable means the vector of claim 7.

9. A host cell containing the vector of claim 7.

10. A method for expressing SEQ ID NO:2 in the recombinant host cell of claim 9, said method comprising culturing said recombinant host cell under conditions suitable for gene expression.

11. A method for producing a protein having the amino acid sequence which is SEQ ID NO:2 in a recombinant host cell of claim 9, comprising culturing said recombinant host cell under conditions suitable for gene expression, and recovering said protein.

12. An isolated nucleic acid fragment, wherein said fragment has a sequence specified herein as SEQ ID NO:4.

13. An isolated nucleic acid fragment that hybridizes to the complementary strand of SEQ ID NO: 1 or SEQ ID NO:3 under high stringency conditions comprising hybridizing at 50° C. to 65° C. in 5×SSPE and 50% formamide, and washing at 50° C. to 65° C. in 0.5×SSPE, and that encodes a protein having the ligand binding activity of *Streptococcus pneumoniae* 454 protein.

14. An isolated nucleic acid fragment that hybridizes to the complementary strand of SEQ ID NO: 1 or SEQ ID NO:3 under low stringency conditions comprising hybridizing at 35° C. to 37° C. in 5×SSPE and 40% to 45% formamide, and washing at 42° C. in 1×–2×SSPE, and that encodes a protein having the ligand binding activity of *Streptococcus pneumoniae* 454 protein.

15. An isolated nucleic acid fragment consisting essentially of a nucleotide sequence encoding a protein having the amino acid sequence that is SEQ ID NO:2.

16. An isolated nucleic acid fragment, wherein said fragment consists essentially of a sequence selected from the group consisting of:

(a) SEQ ID NO: 1;

(b) SEQ ID NO: 3;

(c) a nucleic acid fragment that encodes the same protein as (a) or (b), but which is degenerate in accordance with the degeneracy of the genetic code; and (d) a nucleic acid fragment fully complementary to (a), (b), or (c).

17. The isolated nucleic acid fragment of claim 16, wherein the sequence of said fragment is selected from the group consisting of:

(a) SEQ ID NO:1;

(b) a nucleic acid fragment that encodes the same protein as SEQ ID NO:1, but which is degenerate in accordance with the degeneracy of the genetic code; and (c) a nucleic acid fragment fully complementary to (a) or (b).

18. The isolated nucleic acid fragment of claim 16, wherein the sequence of said fragment is selected from the group consisting of:

(a) SEQ ID NO:3;

(b) a nucleic acid fragment that encodes the same protein as (a) or (b), but which is degenerate in accordance with the degeneracy of the genetic code; and (c) a nucleic acid fragment fully complementary to either of the foregoing.

19. A vector comprising said isolated nucleic acid fragment of claim 16.

20. A host cell containing the vector of claim 19.

21. The vector of claim 19, wherein said isolated nucleic acid fragment is SEQ ID NO:1, operably-linked to a promoter sequence.

22. A method for constructing a recombinant host cell having the potential to express SEQ ID NO:2, comprising introducing into said host cell by any suitable means the vector of claim 21.

23. A host cell containing the vector of claim 21.

24. A method for expressing a protein having the sequence shown in SEQ ID NO:2 in the recombinant host cell of claim 23, comprising culturing said recombinant host cell under conditions suitable for gene expression.

25. A method for producing a protein having the amino acid sequence which is SEQ ID NO:2 in the recombinant host cell of claim 23, comprising culturing said recombinant host cell under conditions suitable for gene expression, and recovering said protein.

26. An isolated nucleic acid fragment, wherein said fragment consists essentially of SEQ ID NO:4.

* * * * *